US010119123B2

(12) United States Patent
Tesar et al.

(10) Patent No.: US 10,119,123 B2
(45) Date of Patent: *Nov. 6, 2018

(54) CELL FATE CONVERSION OF DIFFERENTIATED SOMATIC CELLS INTO GLIAL CELLS

(71) Applicant: CASE WESTERN RESERVE UNIVERSITY, Cleveland, OH (US)

(72) Inventors: Paul J. Tesar, Cleveland, OH (US); Robert H. Miller, Cleveland, OH (US); Fadi J. Najm, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/346,453

(22) Filed: Nov. 8, 2016

(65) Prior Publication Data

US 2018/0051259 A1   Feb. 22, 2018

Related U.S. Application Data

(63) Continuation of application No. 13/280,562, filed on Oct. 25, 2011, now Pat. No. 9,487,757.

(60) Provisional application No. 61/406,670, filed on Oct. 26, 2010.

(51) Int. Cl.
*C12N 15/00* (2006.01)
*C12N 5/074* (2010.01)
*C12N 5/079* (2010.01)

(52) U.S. Cl.
CPC ......... *C12N 5/0696* (2013.01); *C12N 5/0622* (2013.01); *C12N 2501/115* (2013.01); *C12N 2501/135* (2013.01); *C12N 2501/41* (2013.01); *C12N 2501/60* (2013.01); *C12N 2506/1307* (2013.01)

(58) Field of Classification Search
None
See application file for complete search history.

(56) References Cited

U.S. PATENT DOCUMENTS

| | | | |
|---|---|---|---|
| 7,041,507 B1 | 5/2006 | Levesque et al. | |
| 8,206,699 B2 * | 6/2012 | Goldman | C12N 5/0622 424/93.1 |
| 9,487,757 B2 | 11/2016 | Tesar et al. | |
| 2003/0059939 A1 | 3/2003 | Page et al. | |
| 2010/0034785 A1 | 2/2010 | Pedersen et al. | |
| 2013/0022583 A1 | 1/2013 | Wernig et al. | |

FOREIGN PATENT DOCUMENTS

| | | |
|---|---|---|
| WO | 2008/056166 A2 | 5/2008 |
| WO | 2010/108005 A2 | 9/2010 |

OTHER PUBLICATIONS

Windrem et al., Neonatal chimerization with human glial progenitor cells can both remyelinate and rescue the otherwise lethally hypomyelinated shiverer mouse Cell Stem Cell. Jun. 5, 2008; 2(6): 553-565.*
Najm et al Rapid and robust generation of functional oligodendrocyte progenitor cells from epiblast stem cells Nature Methods | vol. 8 No. 11 | Nov. 2011 | 957-962.*
Ishii et al ERK1/ERK2 MAPK Signaling is Required to Increase Myelin Thickness Independent of Oligodendrocyte Differentiation and Initiation of Myelination the Journal of Neuroscience, Jun. 27, 2012 • 32(26):8855-8864 • 8855.*
Benner et al., Depletion of Olig2 in oligodendrocyte progenitor cells infected by Theiler's murine encephalomyelitis virusJournal of NeuroVirology Jun. 2016, vol. 22, Issue 3, pp. 336-348.*
Copray et al., Olig2 overexpression induces the in vitro differentiation of neural stem cells into mature oligodendrocytes. Stem Cells. Apr. 2006;24(4):1001-10.
Du et al., Neural differentiation from embryonic stem cells: which way? Stem Cells Dev. Aug. 2004;13(4):372-81.
Erceg et al., Human Embryonic Stem Cell Differentiation Toward Regional Specific Neural Precursors. Stem Cells. 2009;27:78-87.
Gonzalez et al., Generation of mouse-induced pluripotent stem cells by transient expression of a single nonviral polycistronic vector. Proc Natl Acad Sci U S A. Jun. 2, 2009;106(22):8918-22.
Hu et al., Differentiation of spinal motor neurons from pluripotent human stem cells. Nat Protoc. 2009;4(9):1295-304.
Kierstead et al., Human embryonic stem cell-derived oligodendrocyte progenitor cell transplants remyelinate and restore locomotion after spinal cord injury. J Neurosci. May 11, 2005;25(19):4694-705.
Kim et al., Generation of human induced pluripotent stem cells by direct delivery of reprogramming proteins. Cell Stem Cell. Jun. 5, 2009;4(6)472-6.
Liu et al., Epigenetic modifiers are necessary but not sufficient for reprogramming non-myelinating cells into myelin gene-expressing cells. PLoS One. Sep. 27, 2010;5(9):e13023. 14 pages.
Lu et al., Sonic hedgehog—regulated oligodendrocyte lineage genes encoding bHLH proteins in the mammalian central nervous system. Neuron. Feb. 2000;25(2):317-29.
Lü et al., Cyclosporin A increases recovery after spinal cord injury but does not improve myelination by oligodendrocyte progenitor cell transplantation. BMC Neurosci. Oct. 12, 2010;11:127. 16 pages.
Lü et al., Proliferation and differentiation of oligodendrocyte progenitor cells induced from rat embryonic neural precursor cells followed by flow cytometry. Cytometry A. Aug. 2008;73(8):754-60.
Najm et al., Transcription factor-mediated reprogramming of fibroblasts to expandable, myelinogenic oligodendrocyte progenitor cells. Nat Biotechnol. May 2013;31(5):426-33.

(Continued)

*Primary Examiner* — Maria G Leavitt
(74) *Attorney, Agent, or Firm* — McCarter & English, LLP; Steven G. Davis

(57) ABSTRACT

The present invention relates to the reprogramming of differentiated somatic cells, such as those differentiated cells that arise from embryonic mesoderm, into glial cells. Glial cells produced from this reprogramming are functionally equivalent to glial cells that arise from ectodermal origins.

15 Claims, 4 Drawing Sheets

(56) References Cited

OTHER PUBLICATIONS

Nakashima et al., Astrocyte differentiation mediated by LIF in cooperation with BMP2. FEBS Lett. Aug. 20, 1999;457(1):43-6.

Neman et al., A method for deriving homogenous population of oligodendrocytes from mouse embryonic stem cells. Dev Neurobiol. Jun. 2012;72(6):777-88.

Okita et al., Generation of mouse induced pluripotent stem cells without viral vectors. Science. Nov. 7, 2008;322(5903):949-53.

Stadtfeld et al., Induced pluripotency: history, mechanisms, and applications. Genes Dev. Oct. 15, 2010;24(20):2239-63.

Stadtfeld et al., Induced pluripotent stem cells generated without viral integration. Science. Nov. 7, 2008;322 (5903):945-9.

Stock et al., Transcription Factor-Based Instruction of an Oligodendroglial Fate Using Direct Protein Transduction. Glia. 2009;57:S74-S75. Poster P-200.

Sundberg et al., Production and isolation of NG2+ oligodendrocyte precursors from human embryonic stem cells in defined serum-free medium. Stem Cell Res. Sep. 2010;5(2):91-103.

Vallier et al., Early cell fate decisions of human embryonic stem cells and mouse epiblast stem cells are controlled by the same signalling pathways. PLoS One. Jun. 30, 2009;4(6):e6082.

Vierbuchen et al., Direct conversion of fibroblasts to functional neurons by defined factors. Nature. Feb. 25, 2010;463(7284):1035-41.

Yamanaka, Strategies and new developments in the generation of patient-specific pluripotent stem cells. Cell Stem Cell. Jun. 7, 2007;1(1):39-49.

Zhang et al., Increased myelinating capacity of embryonic stem cell derived oligodendrocyte precursors after treatment by interleukin-6/soluble interleukin-6 receptor fusion protein. Mol Cell Neurosci. Mar. 2006;31(3):387-98. Including Supplementary Materials.

Zhang et al., Neural Differentiation. Human Cell Culture, vol. VI, Embryonic Stem Cells. John R. Masters (Ed.). Springer. Chapter 6, pp. 85-108 (2007).

Zhou et al., Generation of induced pluripotent stem cells using recombinant proteins. Cell Stem Cell. May 8, 2009;4(5):381-4.

International Search Report and Written Opinion for Application No. PCT/US2011/057759, dated May 8, 2012. 14 pages.

United States Non-Final Office Action for U.S. Appl. No. 13/280,543, dated Oct. 3, 2013. 9 pages.

Written Opinion for Application No. PCT/US2011/057762, dated May 7, 2012. 7 pages.

U.S. Appl. No. 13/280,562, filed Oct. 25, 2011, now U.S. Pat. No. 9,487,757.

\* cited by examiner

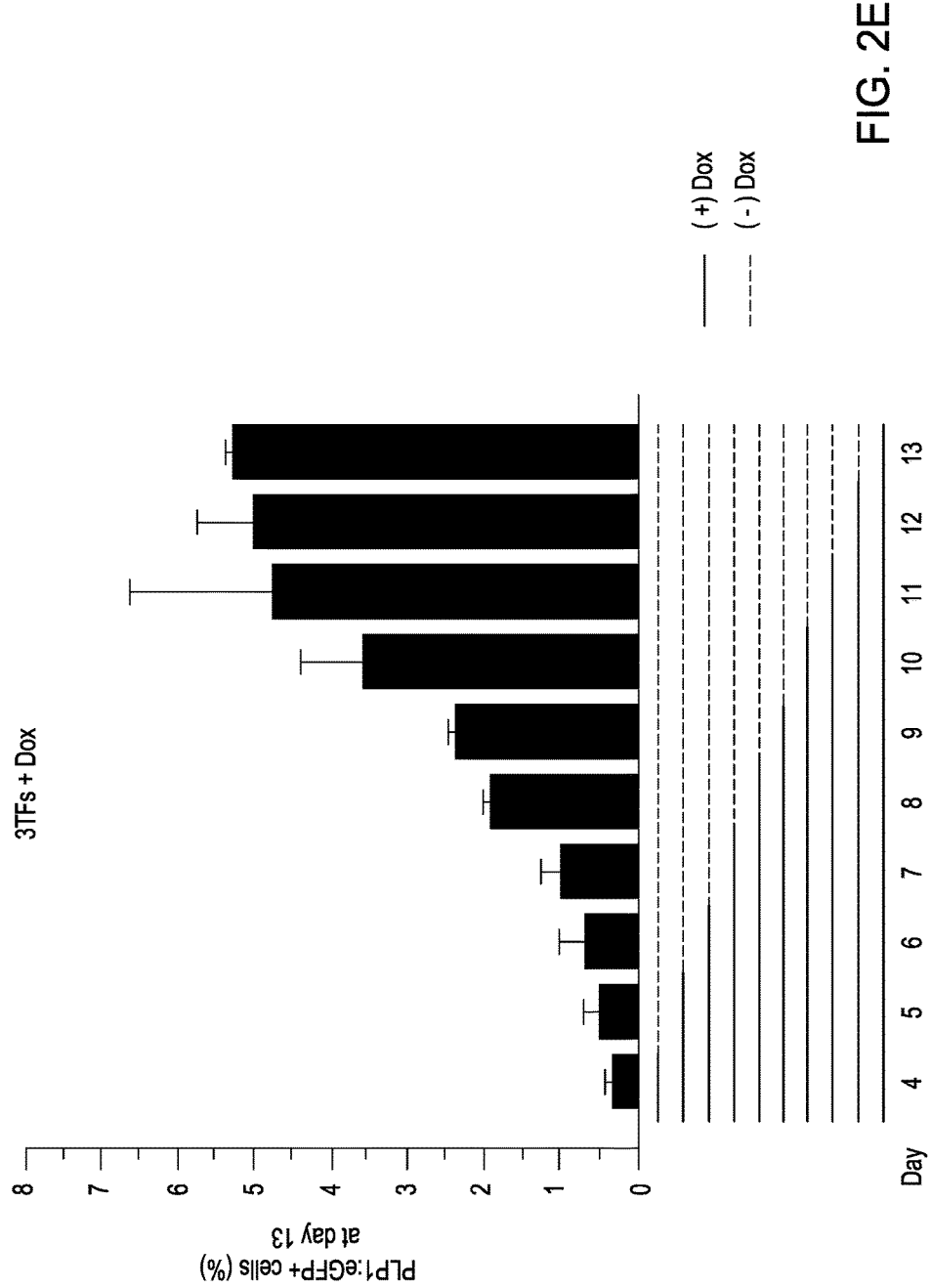

CELL FATE CONVERSION OF DIFFERENTIATED SOMATIC CELLS INTO GLIAL CELLS

CROSS REFERENCE TO RELATED APPLICATIONS

This application is a continuation of U.S. patent application Ser. No. 13/280,562, filed Oct. 25, 2011 and now U.S. Pat. No. 9,487,757, which claims priority from U.S. Provisional Patent Application No. 61/406,670, filed Oct. 26, 2010.

STATEMENT OF GOVERNMENT SPONSORED RESEARCH

This invention was supported in part by grant R21MH087877-01 from the National Institute of Mental Health (NIMH).

FIELD OF THE INVENTION

This invention relates to the field of reprogramming differentiated somatic cells into glial cells.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Multiple sclerosis (MS) is a complex neurological disease characterized by deterioration of central nervous system (CNS) myelin. Myelin is an insulating material composed primarily of lipids that protects nerve fibers—axons—that transmit electric impulses throughout the body. Demyelination of axons in MS results in axon degeneration and neuronal cell death, but more specifically MS destroys oligodendrocytes, specialized glial cells that generate and maintain myelin.

Oligodendrocyte progenitors are generated in ventral areas of the developing brain from a glial progenitor. Oligodendrocyte progenitors actively migrate and proliferate, populating the CNS, eventually maturing to target and extend myelin sheaths along the axons. However, a subpopulation of the oligodendrocyte progenitors remains as resident, undifferentiated cells to play a role if myelin is damaged or deteriorates.

People with MS suffer attacks when T-cells cross the blood brain barrier and attack the myelin sheath that coats axons of the CNS. This disruption should induce the maturation of the subpopulation of oligodendrocyte progenitors that has remained in the CNS to repair damaged myelin. Instead, however, it has been found that people with MS have oligodendrocyte progenitors that tend not to mature into oligodendrocytes after myelin damage, resulting in inadequate myelin repair.

Cell transplantation therapies have been proposed to treat neurodegenerative diseases such as MS, cerebral palsy and Parkinson's Disease; yet wide-spread application of cell-based therapies depends on the availability of sufficient amounts of the proper types of, e.g., oligodendrocyte progenitor cells. One possibility for providing such cells is using embryonic stem cells, for example, see Bjorklund, et al., Nat. Neurosci. 3:537-44 (2000) (studies relating to Parkinson's disease). Embryonic stem cells can be expanded to virtually unlimited numbers and have the potential to generate all types of cells in culture; however, embryonic stem cell-based therapy is complicated by, amongst other things, immune rejection due to immunological incompatibility between the patient and donor. Alternatively, successful generation of cloned stem cells by somatic cell nuclear transfer creates the possibility of generating genetically identical "customized" cells by using donor cells from a patient as the source of the nucleus, thereby eliminating the requirement for immune suppression (see Hochedlinger, et al., N. Engl. J. Med. 349:275-86 (2003)); however, technical and logistical impediments of the nuclear transfer procedure complicate the practical realization of somatic cell nuclear transfer in humans.

Production of large populations of glial cells that are not complicated by patient immunological incompatibility would prove invaluable in studies of CNS myelination, disease modeling, and drug screening. More importantly, promoting remyelination using these cells in cell-based therapies has enormous implications in regenerative medicine. The present invention provides such glial cells, and methods for the generation thereof.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention relates to the reprogramming of differentiated somatic cells into glial cells. Glial cells produced from this reprogramming are functionally equivalent to glial cells that arise from ectodermal origins. The ability to reprogram differentiated somatic cells to produce glial cell populations has enormous implications in studies of CNS myelination, disease modeling, drug screening, and more importantly, regenerative medicine. Thus, one embodiment of the present invention provides a method for producing glial cells comprising: providing somatic cells from a mammalian patient or subject; culturing said somatic cells; and expressing one or more reprogramming factors in said cultured somatic cells to produce a population of glial cells.

In one aspect of the invention, the reprogramming factors comprise one or more reprogramming factors selected from Ascl1, Cenpa, Chd7, Creb312, E2f8, En2, Esco2, Etv6, Fen1, Foxn3, Gm98 (MRF), Grlf1, Gsx1, Hr, Klf13, Lbr, Lcor, Lcor1, Lig1, Mcm2, Mcm5, Mcm6, Mitf, Myb11, Myc11, Myt1, Ncor, Nkx2-2, Nkx6-2, Nr2c1, Olig1, Olig2, Onecut2, Rbpj1, Rev31, Sox10, Sox6, Sox8, St18, Tcf712, Tcfeb, Tmpo, Top2a, Tox3, Wdhd1, Zfp276, Zfp37, Zfp488, Zfp536, Zfp579, Zfpm1, or Zkscan1. In other aspects at least two reprogramming factors selected from Sox 10, Nkx6.2, or Olig2 are used, and in yet other aspects, all three reprogramming factors Sox 10, Nkx6.2, or Olig2 are used. In other aspects, one or more additional reprogramming factors may be used in addition to the one or more reprogramming factors Sox 10, Nkx6.2, or Olig2. For example, one or more of reprogramming factors Olig1, Nkx2.2, ST18, MYT1 or GM98 may be used in addition to the one or more reprogramming factors Sox 10, Nkx6.2, or Olig2. In yet other aspects, all three reprogramming factors Sox 10, Nkx6.2, and Olig2, are used, and one or more of reprogramming factors Olig1, Nkx2.2, ST18, MYT1 or GM98 are used.

In some aspects of the present invention, the patient-derived somatic cells are selected from fibroblasts, adipocytes, chondrocytes, hemocytoblasts, lymphocytes, and the like. In preferred aspects, the patient-derived somatic cells are selected from fibroblasts and hemocytoblasts. In some aspects of the present invention, the reprogramming factors are provided to the somatic cells by delivering a vector driving expression of the one or more reprogramming factors to the somatic cells. In preferred methods of this aspect, a lentiviral vector is employed to deliver the reprogramming factors to the somatic cells, and in some aspects the vector is an inducible vector.

In certain aspects of the present invention, the methods further comprise a sorting step after the delivering or inducing step to sort the population of induced glial cells from the un-induced, non-reprogrammed somatic cells, thus producing an enriched population of reprogrammed glial cells. In some aspects of the invention, the sorting step is accomplished by using one or more markers specific for the patient-derived somatic cells or for the reprogrammed glial cells. In certain aspects, one or more markers specific for glial cells is used for sorting, for example, proteolipid protein 1 (PLP-1), Ki67, A2B2, A2B5, platelet-derived growth factor receptor alpha (PDGFα) receptor, SOX10, Olig1, chondroitin sulphate proteoglycan Ng2, myelin basic protein (MBP), myelin-associated glycoprotein (MAG), myelin oligodendrocyte glycoprotein (MOG), GRM5, CD133, CLN11, ERBB3, ERBB4, TNR or galactocerebrosides (O1, GalC), and the like. In yet other aspects of the invention, the sorting step is accomplished by a selectable marker. In addition or alternatively, reporters for transcriptions factors such as SOX10 and Olig1 may be used to separate the reprogrammed glial cells.

In yet other aspects of the present invention, the methods further comprise a step of expanding the induced, cultured, patient-derived somatic cells after the inducing step or expanding the sorted reprogrammed glial precursor cells after the sorting step.

In another aspect, the invention provides a population of glial cells produced by any of the foregoing methods. The population of glial cells is characterized in that at least 5%, 8%, 10%, 15% or more of the cells in the population express glial-specific cell markers, and the enriched population of glial cells is characterized in that at least 20%, 30%, 40%, 50%, 75%, 80%, 85%, 90%, 95%, 99% or more of the cells in the enriched population express glial-specific cell markers. In one aspect, the patient-derived somatic cells are induced by reprogramming factors Sox 10, Nkx6.2, and Olig2, and subsequently cultured in the presence of sonic hedgehog, noggin, insulin-like growth factor, neurotrophin 3 and/or triiodothryonine for further differentiation. In some aspects, the glial cells are astrocytes, astroglia, or oligodendrocytes, and in other aspects the glial cells are oligodendrocyte progenitor cells.

In yet another aspect of the present invention there is provided a method for producing oligodendrocyte progenitor cells comprising: providing fibroblasts from a patient; culturing the fibroblasts; delivering a vector driving expression of one or more reprogramming factors selected from Sox 10, Nkx6.2, Olig2, Olig1, Nkx2.2, ST18, MYT1 or GM98 to the fibroblasts; inducing expression of the one or more reprogramming factors in the cultured fibroblasts to produce induced fibroblasts, thereby inducing reprogramming of a population of the induced fibroblasts to produce a population of oligodendrocyte progenitor cells. In one aspect of the invention, the reprogramming factors comprise one or more reprogramming factors selected from Sox 10, Nkx6.2, or Olig2. In other aspects at least two reprogramming factors selected from Sox 10, Nkx6.2, or Olig2 are used, and in yet other aspects, all reprogramming factors Sox 10, Nkx6.2, or Olig2 are used. In other aspects, one or more additional reprogramming factors may be used in addition to one or more of reprogramming factors chosen from Sox 10, Nkx6.2, or Olig2. For example, one or more of reprogramming factors Olig1, Nkx2.2, ST18, MYT1 or GM98 may be used in addition to the one or more reprogramming factors Sox 10, Nkx6.2, or Olig2. In yet other aspects, all three reprogramming factors Sox 10, Nkx6.2, and Olig2, are used, and one or more of reprogramming factors Olig1, Nkx2.2, ST18, MYT1 or GM98 are used.

Other aspects of the present invention include pharmaceutical preparations, diagnostic tools and research tools comprising the reprogrammed glial cells of the present invention.

DEFINITIONS

Figure 1:
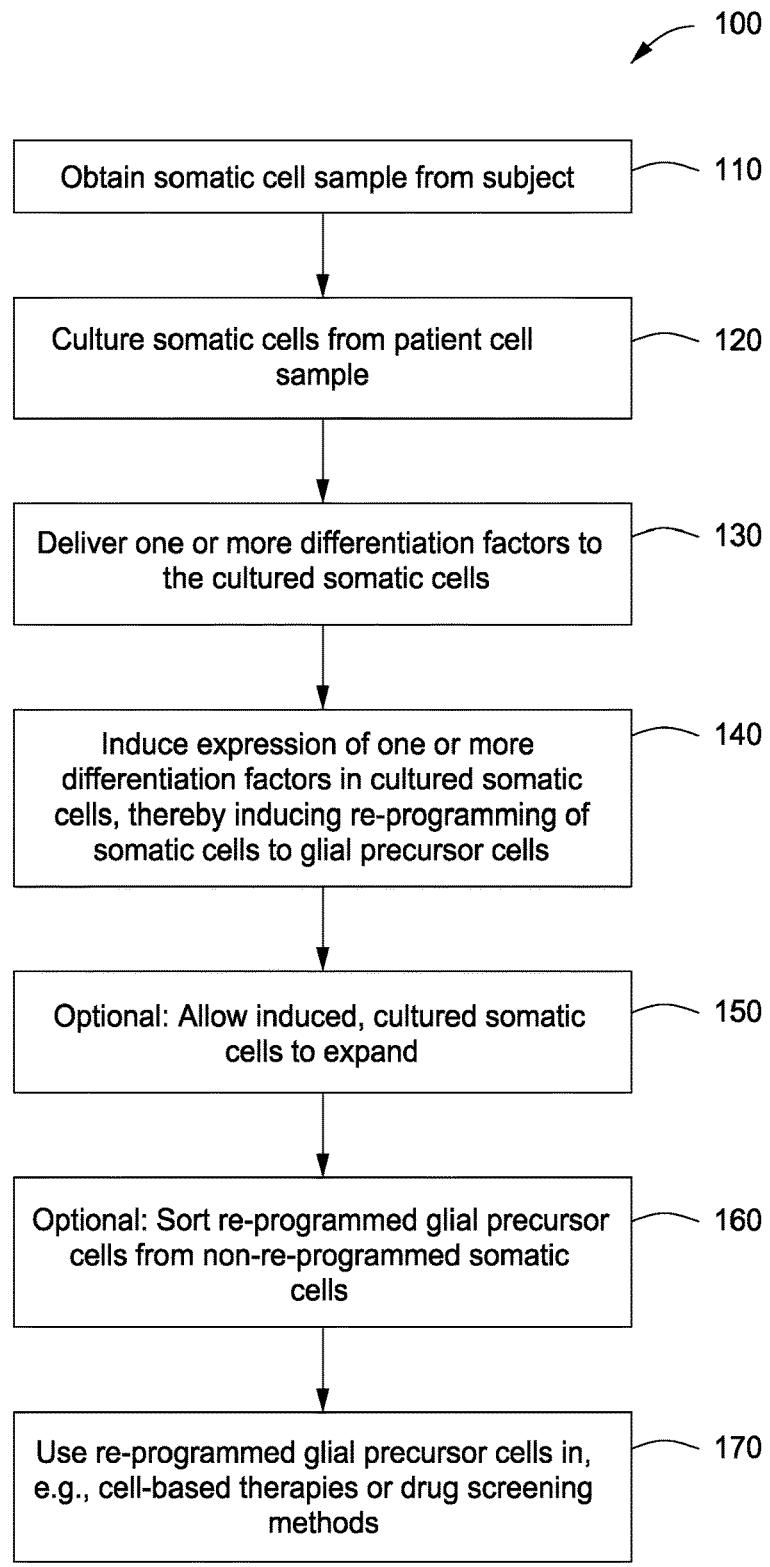
FIG. 1 shows simplified reaction steps of one method according to one aspect of the present invention.

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The terms "astrocytes" and "astroglia" refer to glial cells that anchor neurons to their blood supply. Astrocytes of the present invention refer to both protoplasmic and fibrous astrocytes. Protoplasmic astrocytes have short, thick, highly branched processes and are typically found in gray matter. Fibrous astrocytes have long, thin, less branched processes and are more commonly found in white matter. Astrocytes of the present invention are characterized by expression of one or more marker—glial fibrillary acidic protein (GFAP), S100 beta, glutamine sythetase, GLAST or GLT1—and have at least one astrocytic phenotype selected from structural astrocytic phenotypes or functional astrocytic phenotypes. Astrocytic structural phenotypes include a round nucleus, a "star shaped" body and many long processes that end as vascular foot plates on the small blood vessels of the CNS. Further examples of structural astrocytic phenotypes may be found in the following materials: Reynolds and Weiss, Science 255:1707-1710 (1992); Reynolds, et al., J. Neurosci. 12:4565-4574 (1992); and Kandel, et al. (1991), *Principles of Neuroscience* (Third Ed.) (Appleton & Lange).

A "binding agent" is any molecule that is complementary to one or more regions on a cell of a particular cell fate via association by chemical or physical means. For the purposes of the present invention, the binding agent preferably selectively interacts with a cell surface molecule or intracellular protein or moiety that is unique to cells of a particular cell fate, e.g. oligodendrite precursor cells (OPCs). Examples of binding agents that can be investigated and/or identified using this invention include, but are not restricted to: peptides, proteins (including derivatized or labeled proteins); antibodies or fragments thereof; small molecules; aptamers; carbohydrates and/or other non-protein binding moieties; derivatives and fragments of naturally-occurring binding partners; peptidomimetics; and pharmacophores.

The term "biological process" as used herein includes both normal physiological processes, such as remyelination, neuroprotection, etc. as well as pathological processes, e.g. those involved in diseases and conditions such as autoimmune disease, neurodegenerative disease, diseases involving genetic dysfunction, and the like.

The term "diagnostic tool" as used herein refers to any composition or assay of the invention used in order to carry out a diagnostic test or assay on a patient sample. As a diagnostic tool, the glial cell compositions of the invention may be considered a collection of analyte specific reagents, and as such may form part of a diagnostic test regulated by a federal or state agency. The use of the compositions of the invention as a diagnostic tool is not intended to be related to any use of the composition in the development of therapeutic agents.

As used herein the term "differentiated cells of somatic origin" or "differentiated somatic cells" or "somatic cells" refers to cells originating from the embryonic mesoderm, endoderm, and ectoderm, including bone, cartilage, muscle, connective tissue, skin, vascular tissue, and certain cells of the reproductive, excretory and urinogenital systems.

A "differentiation factor" as that term is used herein refers to any factor or combination of factors that promotes the differentiation or reprogramming of a somatic cell and can include, for example at least one nucleic acid sequence encoding a transcription factor, including but not limited to SOX 10, Nxk6.2, Nxk2.2, Olig1, Olig2, ST18, MYT1 or Gm98.

The term "excipient" refers to an inert substance added to a pharmaceutical composition to further facilitate administration of the cells. Examples, without limitation, of excipients include saline, calcium carbonate, calcium phosphate, various sugars and types of starch, cellulose derivatives, gelatin, vegetable oils and polyethylene glycols.

The term "glial cells" and "glia", are non-neuronal cells that provide support and nutrition, maintain homeostasis, form myelin, and participate in signal transmission in the nervous system. Examples of glial cells of the present invention include but are not limited to astrocytes and oligodendrocyte progenitor cells (OPCs), oligodendrocytes and astrocytes. The term "glial cell" as used herein refers to fully differentiated cells of the glial lineage, such as oligodendrocytes and astrocytes, as well as to precursors to fully differentiated glial cells, such as OPCs.

As used herein, an "inducible promoter" is a promoter that is capable of directly or indirectly activating transcription of one or more DNA sequences or genes (such as genes for reprogramming factors) in response to a "regulatory agent" (e.g., doxycycline), or a stimulus such as heat. In the absence of a "regulatory agent" or stimulus, the DNA sequences or genes will not be transcribed. The term "not transcribed" or "not substantially expressed" means that the level of transcription is at least 50-fold lower than the level of transcription observed in the presence of an appropriate stimulus or regulatory agent; and preferably at least 100-fold, 250-fold, or 500-fold or lower than the level of transcription observed in the presence of an appropriate stimulus or regulatory agent.

As used herein, the term "lentivirus" refers to a group (or scientific genus) of retroviruses that have the ability to incorporate viral DNA or payload into a host genome.

The term "oligodendrocyte" refers to mature, well-differentiated oligodendrocytes. Mature oligodendrocytes may be distinguished from oligodendrocyte progenitor cells both by structural and functional phenotypes. Examples of a mature oligodendrocyte functional phenotype include, but are not limited to one or more, marker expression such as proteolipid protein (PLP) and myelin basic protecin (MBP) expression, myelin-associated glycoprotein (MAG), myelin oligodendrocyte glycoprotein (MOG), in addition to galactocerebrosides (O1, GalC). Examples of mature oligodendrocyte structural phenotypes include, but are not limited to, a branched and ramified phenotype and formation of myelin membranes.

The terms "oligodendrocyte progenitor cells" and "OPCs" as used herein refer to cells that have the capacity to differentiate into oligodendrocytes. Oligodendrocyte progenitor cells may be distinguished from oligodendrocytes both by structural and functional phenotypes. Examples of an OPC functional phenotype include, but are not limited to, a cell that is mitotic (i.e. that can divide and be expanded for three or more passages in culture), has migratory capacity, as well as the potential to differentiate into a myelinating phenotype to effect myelination in vivo and in vitro.

As used herein, the term "regulatory agent" refers to a chemical agent or biological molecule, such as a metabolite, a small molecule, or a physiological or environmental condition such as heat or cold. A recombinant cell containing an inducible promoter may be exposed to a regulatory agent or stimulus by externally applying the agent or stimulus to the cell or organism by exposure to the appropriate environmental condition or biomolecule. Inducible promoters initiate transcription substantially only in the presence of a regulatory agent or stimulus. Examples of inducible promoters include the tetracycline response element and promoters derived from the beta-interferon gene, heat shock gene, metallothionein gene or from steroid hormone-responsive genes.

As used herein, the term "reprogram" or "reprogramming" refers to the process of altering a differentiated state of a somatic cell to take on the identity and function of an alternate cell state.

The term "research tool" as used herein refers to any glial cell composition or assay of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject who may be predisposed to the disease but has not yet been diagnosed as having it; (b) inhibiting the disease, i.e., arresting its development; and (c) relieving the disease, e.g., causing regression of the disease to completely or partially remove symptoms of the disease.

The term "vector" refers to a viral or non-viral carrier nucleic acid molecule (typically a DNA molecule) into which a nucleic acid sequence of interest can be inserted for introduction into a host cell. An "expression vector" is a specialized vector that contains the necessary regulatory regions needed for expression of a nucleic acid sequence of interest in a host cell. In most aspects, the nucleic acid sequence of interest, such as the one or more reprogramming factors described herein, is operably linked to another sequence in the vector. The term "operably linked" means that the regulatory sequences necessary for expression of the differentiation factor are placed in the vector in the appropriate position so as to effect expression of the coding sequence.

As used herein, a population of cells that has been depleted of cells expressing markers of non-glial cells refers to a cell population that has undergone a selection process or reprogramming process that removes at least some of the somatic cells from a population of glial cells. This selection process may be accomplished by any appropriate method that preserves the viability of the glial cells. Preferably depleted populations contain less than 95%, 90%, 80%, 70%, 60%, 50%, 40%, 30%, 20%, 10%, 5%, 2%, 1% or less than 0.1% non-glial cells. Further, cell sorting may be performed on the reprogrammed glial cells population to produce an enriched reprogrammed glial cell population containing less than 80%, 70%, 60%, 50%, 40%, 30%, 20%, 10%, 5%, 2%, 1% or less than 0.1% of non-glial cells.

DETAILED DESCRIPTION OF THE INVENTION

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Butler (2004), *Animal Cell Culture* (BIOS Scientific); Picot (2005), *Human Cell Culture Protocols* (Humana Press), Davis (2002), *Basic Cell Culture*, Second Ed. (Oxford Press); Lanza, et al., (Eds.) (2009), *Essentials of Stem Cell Biology*, Second Ed. (Elsevier Academic Press); Lanza, (Ed.) (2009), *Essential Stem Cell Methods* (Elsevier Academic Press); and Loring, et al. (Eds.) (2007), *Human Stem Cell Manual* (Elsevier Academic Press); Freshney (2010), *Culture of Animal Cells* (John Wiley & Sons); Ozturk and Hu (2006), *Cell Culture Technology for Phamaceutical and Cell-Based Therapies* (CRC Press); Sambrook and Russell (2006), *Condensed Protocols from Molecular Cloning: A Laboratory Manual*; and Sambrook and Russell (2002), *Molecular Cloning: A Laboratory Manual* (both from Cold Spring Harbor Laboratory Press); Stryer, L. (1995) *Biochemistry*, Fourth Ed. (W.H. Freeman); Gait (1984), *"Oligonucleotide Synthesis: A Practical Approach"* (IRL Press); Nelson and Cox (2000), *Lehninger, Principles of Biochemistry*, Third Ed. (W. H. Freeman); and Berg et al. (2002) *Biochemistry*, Fifth Ed. (W.H. Freeman); all of which are herein incorporated in their entirety by reference for all purposes.

Note that as used herein and in the appended claims, the singular forms "a," "an," and "the" include plural referents unless the context clearly dictates otherwise. In addition, a reference to "sorting" or "inducing" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The present invention relates to the reprogramming of differentiated somatic cells—such as those differentiated cells that arise from the mesoderm—into glial cells. Glial cells produced from this reprogramming are functionally equivalent to glial cells that arise from ectodermal origins. The ability to reprogram differentiated, somatic cells to produce glial cell populations has enormous implications in studies of CNS myelination, disease modeling, drug screening, and more importantly, for use in regenerative medicine.

FIG. 1 shows simplified reaction steps of a method 100 according to one aspect of the present invention. In brief, in a first step a somatic cell sample is obtained from a mammalian subject or patient 110. In a second step, the patient-derived somatic cell samples are cultured 120. Next, one or more reprogramming factors are delivered to the cultured somatic cells 130. Expression of the reprogramming factors is then induced in the patient-derived somatic cells, thereby reprogramming the somatic cells to glial cells 140. The induced, cultured, reprogrammed patient-derived somatic cells optionally are then allowed to expand 150, and the entire population of cells optionally is then sorted to separate uninduced, non-reprogrammed somatic cells from induced, reprogrammed glial cells to produce an enriched population of glial cells 160. The population of induced, reprogrammed glial cells may then be used in cell-based therapies, or drug screening, myelination or disease modeling experiments 170.

Looking at each step of method 100 in detail, first step 110 requires a patient-derived cell sample be collected. The methods of the present invention produce reprogrammed cell populations derived from a patient's own cells, thereby eliminating complications related to immunological incompatibility. Patient-derived somatic cell samples can be collected from skin, connective tissue, blood or bone marrow, where sample collection techniques are known in the art. Those with skill in the art will appreciate and understand selection of the particular type of sample required and an appropriate procedure for sample preparation (see, e.g., Tietz, Burtis, et al., (Eds.) (2006), *Textbook of Clinical Chemistry and Molecular Diagnostics*, (4th Ed.); Venkatesh Iyengar, et al. (1998), *Element Analysis of Biological Samples: Principles and Practices*; and Wells, D. (2002), *High Throughput Bioanalytical Sample Preparation (Progress in Pharmaceutical and Biomedical Analysis)*, each of which is incorporated by reference).

The second step 120 involves culturing the patient-derived somatic cells, preferably in vitro. Cell culture techniques are well known in the art, with reference to such text books as Butler (2004), *Animal Cell Culture* (BIOS Scientific); Picot (2005), *Human Cell Culture Protocols* (Humana Press); Davis (2002), *Basic Cell Culture*, Second Ed. (Oxford Press); Freshney (2010), *Culture of Animal Cells* (John Wiley & Sons); and Ozturk and Hu (2006), *Cell Culture Technology for Phamaceutical and Cell-Based Therapies* (CRC Press). For example, culture of primary fibroblasts from skin typically involves mincing the tissue sample in BME fibroblast medium or DMEM (Dulbecco's MEM) and collagenase or trysin (approximately in a 6:1 ratio), placing the slurry in a test tube at 37° C. for 14-24 hours, centrifuging the tube at 600 g for 10 minutes, removing the supernatant, resuspending the cell pellets in cell culture medium and plating the resuspended cells in tightly closed cell culture flasks in a $CO_2$ incubator at 37° C. overnight. The next day, the lid of the flasks is loosened to expose the medium to the $CO_2$ atmosphere, and the cells are then allowed to grow, with medium changed and cells split as needed.

In the third step, 130, one or more reprogramming factors are delivered to the cultured patient-derived somatic cells. Conventional viral and non-viral based gene transfer methods can be used to introduce nucleic acids encoding the reprogramming factors into the somatic cells in vitro. Non-viral vector delivery systems include DNA plasmids, naked nucleic acids, modified RNA molecules that can be directly translated, and nucleic acids complexed with a delivery vehicle such as poloxamers or liposomes. Methods of non-viral delivery of nucleic acids encoding the reprogramming factors provided herein include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those disclosed in Felgner, WO 91/17424 and WO 91/16024. Further, proteins can be directly transfected into cells. In yet another alternative, agents such as small molecules may be delivered to the patient-derived somatic cells that stimulate endogenous production of reprogramming factors.

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); and U.S. Pat. Nos. 4,186,183, 4,217,344, 4,235,871, 4,261,975, 4,485,054, 4,501,728, 4,774,085, 4,837,028, and 4,946,787).

Alternatively, the use of RNA or DNA viral-based systems for the delivery of nucleic acids encoding the reprogramming factors takes advantage of highly-evolved processes for targeting a virus to cells and trafficking the viral payload to the nucleus. Various viral delivery vehicles, as are known in the art, can be used to introduce a nucleic acid (e.g., a nucleic acid encoding a differentiation factor) into a cell. The choice of delivery vehicle depends upon a number of factors, including but not limited to the size of the nucleic acid to be delivered and the desired target cell. Conventional viral based systems for the delivery of nucleic acids such as the reprogramming factors to be delivered in the methods herein may include retroviral, lentivirus, adenoviral, adeno-associated and herpes simplex virus vectors for gene transfer. Viral vectors are currently the most efficient and versatile method of gene transfer in target cells. Integration in the host genome is possible with the retrovirus, lentivirus, and adeno-associated virus gene transfer methods, often resulting in long-term expression of the inserted transgene.

The tropism of a retrovirus can be altered by incorporating foreign envelope proteins, expanding the potential target population of target cells. Lentiviral vectors are retroviral vectors that are able to transduce or infect nondividing cells and typically produce high viral titers. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), feline immune deficiency virus (FIV), equine immune deficiency virus (EIV) and combinations thereof.

Lentiviral delivery vehicles have been described, for example, in U.S. Pat. Nos. 6,312,682 and 6,669,936 and in U.S. Patent Application Publication No. 2002/0173030 and can be used, e.g., to introduce transgenes into fibroblasts and other cells. As mentioned, lentiviruses are capable of integrating a DNA copy of their RNA genome into the genome of a host cell. See, e.g., Ory et al., Proc. Natl. Acad. Sci. USA 93:11382-11388 (1996); Miyoshi et al., J. Virology 72:8150-8157 (1998); Dull et al., J. Virol. 72:8463-8471 (1998); Zuffery et al., J. Virol. 72:9873-9880(1998); Follenzi et al., Nature Genetics 25:217-222 (2000) and Delenda, J. Gene Medicine 6:S125-S138 (2004). In certain lentiviral vehicles, this integration function has been disabled to generate non-integrating lentivirus vehicles. See, e.g., Poon et al., J. Virology 77:3962-3972 (2003); and Vargas et al., Human Gene Therapy 15:361-372 (2004). The use of both integrating and non-integrating lentiviral vectors for transduction of hematopoietic stem cells has been described by Haas et al., Mol. Therapy 2:71-80 (2000), and the use of lentiviral vectors for transduction of fibroblasts has been described in Ieda, et al., Cell 142:375-86 (2010) and Vierbuchen, et al., Nature 463:1035-41 (2010), both of which are incorporated in their entirety herein.

Use of recombinant adeno-associated viral vectors (rAAV) is an alternative gene delivery system to lentiviral systems, and is based on the defective and nonpathogenic parvovirus adeno-associated type 2 virus. Vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (See Wagner et al., Lancet 351:9117 1702-3 (1998), and Kearns et al., Gene Ther. 9:748-55 (1996)). Replication-deficient recombinant adenoviral vectors may be engineered such that a transgene replaces the Adenoviral E1a, E1b, and E3 genes; subsequently the replication defective vector is propagated in human 293 cells that supply deleted gene function in trans. Adenoviral vectors can transduce multiple types of tissues in vitro, including nondividing, differentiated cells such as those found in the liver, kidney and muscle system tissues. Conventional adenoviral vectors have a large carrying capacity.

Herpes simplex virus vehicles, which are capable of long-term expression in neurons and ganglia, have been described and may also be used to deliver reprogramming factors to the subject- or patient-derived somatic cells. See, e.g., Krisky et al., Gene Therapy 5(11):1517-1530(1998); Krisky et al., Gene Therapy 5(12):1593-1603 (1998); Burton et al., Stem Cells 19:358-377 (2001); and Lilley et al., J. Virology 75(9):4343-4356 (2001).

Packaging cells are used to form virus particles that are capable of infecting a host cell such as a fibroblast. Such cells include 293 cells and Psi2 cells or PA317 cells. Viral vectors are usually generated by a producer cell line that packages a nucleic acid vector into a viral particle. The vectors typically contain the minimal viral sequences required for packaging and subsequent integration into a host, with other viral sequences being replaced by an expression cassette for the differentiation factor to be expressed. The missing viral functions are supplied in trans by the packaging cell line.

Reprogramming factors contemplated for use in the methods of the present invention include SOX-10, Nkx6.2, Olig2, Olig1, Nkx2.2, ST18, MYT1 or MRF. Transcription factor SOX-10 is a protein that in humans is encoded by the SOX10 gene. The SOX10 gene encodes a member of the SOX (SRY-related HMG-box) family of transcription factors involved in the regulation of embryonic development and in the determination of cell fate. The encoded protein may act as a transcriptional activator after forming a protein complex with other proteins. SOX-10 acts as a nucleocytoplasmic shuttle protein and is important for neural crest and peripheral nervous system development. Nkx6.2, or NK6 transcription factor related, locus 2 (also known as NKX6B, NKX homeobox 2, and GTX), has been shown to be involved in the regulation of oligodendocyte myelination. Olig2 is oligodendrocyte transcription factor 2, a basic helix-loop-helix transcription factor. Expression of Olig2 is predominantly restricted to the CNS and is a regulator of ventral neuroectodermal pregenitor cell line fate and may be required for oligodendrobyte and motor neuron development. Oligo1 is oligodendrocyte transcription factor 1, also a basic helix-loop-helix transcription factor.

Nkx2.2, or NK2 transcription factor related, locus 2 (also known as NKX2B, homeobox protein NK-2 homolog B) is a homeobox domain-containing protein and may be involved in the morphogenesis of the central nervous system. Also, this protein is thought to play a role in axonal guidance. ST18 is also known as suppression of tumorigenicity protein 18, a zinc finger protein (also known as KIAA0535 or ZNF387) that represses basal transcription activity from target promoters. MYT1, myelin transcription factor 1, is a protein that in humans is encoded by the MYT1 gene, and is a member of a family of neural-specific, zinc finger-containing DNA-binding proteins. MYT1 binds to the promoter regions of proteolipid proteins of the CNS, playing a role in the development of the CNS. MRF is myelin gene regulatory factor, also known as Gm98 (myelin gene regulatory factor predicted gene 98).

Once one or more reprogramming factors has been delivered to the cultured somatic cells, expression of the one or more reprogramming factors is initiated to induce reprogramming of the patient-derived somatic cells into glial cells in step 140. In some aspects of the present invention, the one or more reprogramming factors to be expressed are under control of one or more constitutive promoters, and expression of the reprogramming factors is constitutive and need not be actively induced. In other aspects of the present invention, expression of the one or more reprogramming factors is under control of an inducible promoter system. Inducible promoters that may be used in performing the methods of the present invention include those regulated by hormones and hormone analogs such as progesterone, ecdysone and glucocorticoids as well as promoters which are regulated by tetracycline, heat shock, heavy metal ions, interferon, and lactose operon activating compounds. For a review of these systems see Gingrich and Roder, Ann. Rev. Neurosci. 21:377-405 (1998). Tissue-specific expression has been well characterized in the field of gene expression and tissue-specific and other inducible promoters are well known in the art.

In an inducible expression system, control of expression of the one or more reprogramming factors is achieved by contacting the patient-derived somatic cell transformed or transfected with one or more reprogramming factors with a regulatory agent (e.g., doxycycline) or other inducing agent. Contacting the patient-derived somatic cell with a regulatory agent induces expression of the one or more reprogramming factors, while withdrawal of the regulatory agent inhibits expression. However, it should be recognized by one skilled in the art that in other inducible vectors, the opposite is true, that is, the regulatory agent inhibits expression and removal permits expression. Induction of expression is necessary for only a certain portion of the reprogramming process. While the time necessary for induction of expression will vary with the somatic cell type used, it is advisable to detect glial cells in at least a subset of the somatic cells in the culture prior to stopping the induction stimulus. However, it is well within the abilities of one skilled in the art through routine experimentation to identify an appropriate time necessary to treat the somatic cells with an induction stimulus.

Once expression of one or more reprogramming factors has been achieved in a population of the patient-derived somatic cells—inducing reprogramming of the somatic cells into glial cells—the reprogrammed cell population is optionally allowed to expand 150. Expansion is performed under conditions appropriate for the reprogrammed cell type, with the growth medium supplemented appropriately and changed and the cells split as needed.

When an adequate population of reprogrammed cells is achieved, the induced, reprogrammed glial cells may, optionally, be sorted from the uninduced, non-reprogrammed patient-derived somatic cells 160. In one aspect, the cells are sorted using a using a fluorescence activated cell sorter (FACS). Fluorescence activated cell sorting (FACS) is a known method for separating particles, including cells, based on the fluorescent properties of the cells. See, e.g., Kamarch, Methods Enzymol 151:150-165 (1987). Laser excitation of fluorescent moieties in the individual cells results in a small electrical charge allowing electromagnetic separation of positive and negative cells from a mixture. For example, an antibody or ligand used to detect a glial cell antigenic determinant present on the cell surface of the reprogrammed glial cells is labeled with a fluorochrome, such as FITC or phycoerythrin. The cells are incubated with the fluorescently-labeled antibody or ligand for a time period sufficient to allow the labeled antibody or ligand to bind to glial cells. The cells are processed through a cell sorter, allowing separation of the cells of interest from other cells.

Separation of the reprogrammed glial cells from the non-reprogrammed somatic cells may be achieved by using markers specific to glial cells such as PLP-1 (proteolipid protein 1, a transmembrane proteolipid protein that is the predominant myelin protein present in the CNS), Ki67 proliferation marker, cell surface markers A2B2 or A2B5, nestin, platelet-derived growth factor alpha receptor, chondroitin sulphate proteoglycan NG2, myelin-associated glycoprotein (MAG), myelin oligodendrocyte glycoprotein (MOG), GRM5, CD133, CLN11, ERBB3, ERBB4, TNR, in addition to galactocerebrosides (O1, GalC) and the like. See, e.g., Roy, et al., J. Neurosci. 19:9986-95 (1999) and Windrem, et al., J. Neurosci., 69:966-75 (2002). In addition or alternatively, reporters for transcriptions factors such as SOX10 and Olig1 may be used to separate the reprogrammed glial cells.

Alternatively, magnetic beads can be also used to separate the reprogrammed glial cells from the non-reprogrammed somatic cells in some aspects of the present invention. For example, glial cells can be sorted from somatic cells using a magnetic activated cell sorting (MACS) technique, a method for separating cells based on their ability to bind magnetic beads. A variety of useful modifications can be performed on the magnetic microspheres, including covalent addition of an antibody which specifically recognizes a glial cell-surface molecule or hapten, some of which have been described herein. A magnetic field is then applied to physically manipulate the selected beads. In a specific aspect, antibodies to a glial cell surface marker are coupled to magnetic beads. The beads are then mixed with the glial cell culture to allow binding. Cells are then passed through a magnetic field to separate out cells having the glial cell surface markers of interest. These cells can then be isolated and cultured to produce an enriched population of reprogrammed glial cells. Alternatively, the reprogrammed glial cells may be sorted from the uninduced, non-reprogrammed patient-derived somatic cells by selecting for, e.g., cell surface molecules or other antibodies of ligands associated with the patient-derived somatic cells by various techniques, or by immunopanning or selection via, e.g., antibiotic resistance or other selectable marker.

Once a population of reprogrammed glial cells is obtained, the cells may be used in CNS myelination, disease modeling, drug screening, and more importantly, regenerative medicine 170.

The reprogrammed glial cell populations created using the methods of the invention can be used for research, development and therapeutic intervention in multiple disease states involving glial cells, and in particular diseases involving the CNS. Exemplary diseases are described in more detail below.

Multiple sclerosis (MS), a progressive, neurodegenerative disease of the CNS, occurs most often in a relapsing/remitting form, in which a period of demyelination is followed by a period of functional recovery (Weiner, Ann. Neurol. 65:239-248 (2009)). The recovery stage involves remyelination via the migration and maturation of oligodendrocyte progenitor cells (Chari, Int. Rev. Neurobiol. 79:589-620 (2007)). However, as the disease progresses, remyelination fails with continuous loss of function (Blakemore and Keirstead, J. Neuroimmunol. 98:69-76 (1999)). Possible explanations for the failure of intact axons to become remyelinated include defects in oligodendrocyte progenitor cell recruitment to the site of demyelination or in oligodendrocyte progenitor cell differentiation into myelinating oligodendrocytes. Although studies indicate that both aspects of oligodendrocyte progenitor cell biology are altered in MS, the molecular mechanisms that orchestrate these processes within the adult CNS are incompletely understood.

Other conditions mediated by a loss of myelin include an ischemic demyelination condition, an inflammatory demyelination condition, a pediatric leukodystrophy, mucopolysaccharidosis, perinatal germinal matrix hemorrhage, cerebral palsy, periventricular leukoinalacia, radiation-induced conditions, mental illness such as Schizophrenia and subcortical leukoencephalopathy due to various etiologies. Ischemic demyelination conditions include cortical stroke, Lacunar infarct, post-hypoxic leukoencephalopathy, diabetic leukoencephalopathy, and hypertensive leukoencephalopathy. Inflammatory demyelination conditions include multiple sclerosis, Schilder's Disease, transverse myelitis, optic neuritis, post-vaccination encephalomyelitis, and post-infectious encephalomyelitis. Pediatric leukodystrophy conditions include lysosomal storage diseases (e.g., Tay-Sachs Disease), Cavavan's Disease, Pelizaeus-Merzbacher Disease, and Crabbe's Globoid body leukodystrophy.

An example of mucopolysaccharidosis is Sly's Disease. Radiation-induced conditions include radiation-induced leukoencephalopathy and radiation-induced myelitis. Etiologies causing subcortical leukoencephalopathy include HIV/AIDS, head trauma, and multi-infarct states.

In one particular aspect of the present invention, the reprogrammed glial cells comprise oligodendrocyte progenitors or oligodendrocytes and the medical condition to be treated is associated with insufficient myelination.

According to still further features in the described preferred aspects the reprogrammed glial cells comprise astrocytes and the medical condition is selected from the group consisting of Alexander disease, epilepsy, Alzheimer's disease, spinal cord injury, traumatic brain injury, amyotrophic lateral sclerosis and neurogenesis deficiencies.

The mammalian subject treated with reprogrammed glial cells in accordance with the present invention is preferably a human and, most preferably, an adult or post-natal human. Numerous methods for introducing generated cells into a subject may be used. Thus, an important aspect of the present invention relates to a method of treating a subject having a condition mediated by a loss of myelin or a loss of oligodendrocytes by administering to the subject a pharmaceutical composition comprising reprogrammed glial cells under conditions effective to treat the condition mediated by a loss of myelin or a loss of oligodendrocytes.

For injection, the active ingredients of the pharmaceutical composition may be formulated in aqueous solutions, preferably in physiologically compatible buffers such as Hank's solution, Ringer's solution, or physiological salt buffer. Such injections include intraparenchymal injections into the affected portion of the brain as well as introduction of the cells at a more distal site in the brain, brain stem or CNS, with migration to the affected part of the brain.

Administration of the pharmaceutical composition involves cell doses ranging from $1 \times 10^4$ to $1 \times 10^9$, depending on the extent of desired remyelination. Dosage amount and injection intervals may be adjusted individually to levels of the active ingredient which are sufficient to effectively regulate remyelination by the implanted cells. Dosages necessary to achieve the desired effect will depend on individual characteristics and route of administration.

Depending on the severity and responsiveness of the condition to be treated, dosing can be a single administration or a plurality of administrations, with course of treatment lasting from several days to several weeks until diminution of the disease state is achieved. The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition. For example, a treated MS patient will be administered an amount of cells sufficient to alleviate the symptoms of the disease, based on the monitoring indications.

The reprogrammed glial cells of the present invention may be co-administered with excipients, or in a "cocktail" with therapeutic agents useful in treating neurodegenerative disorders, such as gangliosides; antibiotics, neurotransmitters, neurohormones, toxins, neurite promoting molecules; or antimetabolites and precursors of neurotransmitter molecules. Additionally, the reprogrammed glial cells of the present invention may be co-administered with other cells. Following transplantation, the reprogrammed glial cells of the present invention preferably survive in the diseased area for a period of time (e.g., at least 6 months), such that a therapeutic effect is observed.

In one aspect of the present invention, reprogrammed glial cells are administered to a subject after administering radiation and before demyelination has occurred. The purpose of radiation administration is to treat primary and metastatic tumors of the central nervous system. In certain circumstances, including those in which the oligodendrocyte progenitor or oligodendrocyte deficiency is coupled with a loss of neurons, it may be desirable to transplant mixed cell populations, such as mixtures of oligodendrocyte progenitor cell populations and neurons or neuronal precursors. The differentiated cells of the invention can thus be co-introduced with neurons or neuronal precursors, such as those produced as described in U.S. Publication No. 20100021437, which is incorporated herein by reference. In a specific aspect, it is thus preferred that a subject receive both oligodendrocyte progenitor and oligodendrocyte cell populations and neurons to effect directed differentation.

Generally, any method known in the art can be used to monitor success of transplantation of the reprogrammed glial cells. For example, MRI can be used for visualizing brain white matter and studying the burden of demyelinating lesions as currently practiced for monitoring MS patients. Additionally, magnetization transfer contrast can be used to monitor remyelination (see, e.g., Deloire-Grassin, J. Neurol. Sci. 178:10-16 (2000)). Magnetic resonance spectroscopy measurement of N-acetyl-aspartate levels can be used to assess impact on local neuron/axon survival. Using paramagnetic particles to label the reprogrammed glial cells before transplantation allows cellular dispersion to be tracked by MRI. Serial neurophysiology is useful for monitoring conduction. The optic nerve has particular advantages in this respect.

Other approaches to more generalized neurophysiological assessment are described in Leocani et al., Neurol Sci. 21(4 Suppl 2):5889-91 (2000), which may be useful for interventions aimed at multifocal or more diffuse myelin repair. Notwithstanding, it is appreciated that clinical improvement may also be assessed. Demyelination causes alterations of stature (trembling, shivering) and locomotion. Children with leukodystrophies have motor and intellectual retardation. Electrophysiological measures of sensory and motor nerve conductivity, for example H-wave measurements, are classical methods used in monitoring neuropathies linked to demyelinating peripheral lesions (Lazzarini et al., (Eds.) (2004), *Myelin biology and disorders* (Elsevier Academic Press)).

One significant use of the induced glial cell populations of the invention is as a research tool specifically for the discovery and development of therapeutic products for modulation of a biological process involved in a disease, disorder and/or physiological behaviors such neuronal repair. The research tool may be useful in various aspects of drug discovery and investigation, including without limitation the initial identification of a drug candidate, the confirmation of activity of a drug candidate; and the identification of activity in an existing pharmaceutical product.

Another use of the composition is as a research tool specifically used as a diagnostic tool to detect the presence or absence of molecules known to be necessary for the modulation of a biological process involved in a disease or disorder.

Thus, in one aspect the invention includes research tools comprising the compositions of the invention, and uses of such research tools in identification, investigation and/or confirmation of activity of selective binding agents that are useful as therapeutic agents. The present invention thus encompasses binding agents that are isolated using the method of the invention and uses of such binding agents in either a therapeutic or a diagnostic setting.

Thus, according to yet another aspect of the present invention there is provided a method of determining an effect of a treatment on CNS functionality, the method comprising subjecting a cell of the present invention to a treatment or binding agent (e.g., drug, condition such as electrical treatment and an irradiation treatment); and determining at least one of a structural or functional phenotype of the treated cell as compared to an untreated cell, thereby determining an effect of the treatment on CNS functionality. The cells of the present invention can be used to identify and optimize treatments capable of restoring the neural function via activity of glial cells, and hence can be used to identify and optimize drugs suitable for treating neural disorders (e.g., including treatment methods envisaged by the present invention).

Furthermore, determining the effect of a treatment (either directed to diseases of the CNS or any other tissue) on neural functionality can be used to assess the toxicity of such clinical treatments on CNS function. Thus, this aspect of the present invention can be utilized to determine the therapeutic and toxic effects of various treatments, such as drug treatments, and electrical treatments, on neural function via activity of glial cells.

The present invention can be also utilized to obtain gene expression profiles and changes thereof in cells of the present invention subjected to a treatment. Thus, the method according to this aspect of the present invention can be used to determine, for example, gene expression pattern changes in response to a treatment.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

In general, the methods described herein and in the specific examples below are applicable to mammalian pluripotent cells; however, the timing required for the various differentiation steps described herein may vary between mammals.

Example 1: Generation of OPCs from Fibroblasts

Isolation of PLP1:GFP/rtTA Fibroblasts.

Both mouse embryonic fibroblasts (MEFs) and mouse lung fibroblasts (MLFs) were generated from timed natural matings between PLP1:eGFP mice and reverse tetracycline-controlled transactivator (rtTA) mice (B6.Cg-Gt(ROSA) 26Sortm1 (rtTA*M2) Jae/J; Jackson Laboratory) at embryonic day 13.5 (E13.5). For MEFs, the head, spinal cord, and all internal organs were carefully removed to eliminate contamination with any neural precursors. The remainder of the tissue was cut into small pieces and dissociated using 0.125% trypsin-EDTA (Invitrogen). Cells were expanded for one passage and cryopreserved for future use. MLFs were isolated by dissociating pooled lung lobes using 0.125% trypsin-EDTA, expanded for two passages, and cryopreserved for future use. Both MEFs and MLFs were derived in DMEM supplemented with 10% fetal bovine serum (FBS), 2 mM glutamax, 1× nonessential amino acids, and 0.1 mM 2-mercaptoethanol.

Selection of Eight Transcription Factors (8 TFs).

The following publically available datasets were utilized: GSM241931, GSM241936, GSM241929, GSM241937, GSM241934, and GSM241933 13. Putative transcription factors were filtered by selecting genes with both a 'GO cellular component term' "nucleus" and a 'GO molecular function term' "DNA binding." Transcription factors that were enriched >3-fold in a particular lineage were selected and cross-referenced with microarray data of stem cell-derived OPCs and oligodendrocytes. Data were then z-scored and heatmapped in R using the heatmap.2 function of the gplots package.

Production of Lentivirus.

Mouse coding regions of MRF, Myt1, Nkx2.2, Olig1, ST18, Nkx6.2, Olig2 and Sox10 were cloned into the pLVX-Tight-Puro vector (Clontech). VSV-G pseudotyped lentivirus was generated according to the manufacturer's protocol using the Lenti-X HT Packaging Mix and Lenti-Phos or Cal-Phos Mammalian Transfection Kit (all from Clontech). 293T cells (Clontech) cultured on rat tail collagen I coated plastic-ware (BD Biosciences) were seeded with between 6.0 and $8.5 \times 10^4$ cells/cm$^2$ and transfected sicteen hours later. Individual supernatants containing virus were harvested and filtered with 0.45 μm PVDF membrane (Millipore) 48-72 hours later.

Induced Oligodendrocyte Progenitor Cell (iOPC) Generation.

MEFs or MLFs were seeded at $1.3 \times 10^4$ cells/cm$^2$ and infected with fresh lentivirus supplemented with polybrene (8 μg/ml) four times over a two day period. The end of the virus infection period was termed 'day 0'. Cells were either uninduced or induced with 2 μg/ml doxycycline (Clontech) for three days in MEF culture conditions. Cells were then lifted with TrypLE Select and either frozen or seeded at $2.0 \times 10^4$ cells/cm$^2$ on Nunclon-Δ plates pre-coated with 0.1 mg/ml poly-L-ornithine (Sigma) and 10 μg/ml laminin (Sigma; L2020) and cultured in OPC medium (DMEM/F12 (Invitrogen, 11320) supplemented with 1×N2 (R&D Systems), 1×B-27 without vitamin A (Invitrogen), 2 mM Glutamax (Invitrogen), 200 ng/ml SHH (R&D Systems), 20 ng/ml FGF2 (R&D Systems), and 20 ng/ml PDGF-AA (R&D Systems)). Media was changed every two days. iOPCs (PLP1:eGFP+ cells) were typically sorted between days 14-21 using a FACSAria (BD Biosciences) and further expanded in OPC medium with FGF2, PDGF-AA, and SHH. iOPCs were passaged every 3-5 days with TrypLE Select (Invitrogen) and were readily frozen/thawed in DMEM supplemented with 10% FBS and 10% DMSO (Sigma).

Induced Oligodendrocyte Progenitor Cells (iOPC) Differentiation to Induced Oligodendrocyted (iOLs).

For differentiation of iOPCs into iOLs, cells were plated at $2.2 \times 10^4$ cells/cm$^2$ (iOPCs from MLFs at $1.1 \times 10^4$ cells/cm$^2$) and induced with OPC medium supplemented with 0.4 ng/ml T3 (Sigma), 200 ng/ml SHH, 100 ng/ml Noggin, 10 μM cAMP, 100 ng/ml IGF, and 10 ng/ml NT3. Cultures were fixed after three days and stained for MBP.

Immunocytochemistry.

Cells were prepared for immunostaining by fixation in 4% paraformaldehyde (Electron Microscopy Sciences) for 15 minutes and subsequent permeabilization for 10 minutes with 0.2% Triton-X in PBS. Cells were then blocked for nonspecific binding with filtered 10% normal goat (Abcam) or 10% donkey serum (Abcam) in PBS for 1-2 hours at room temperature. Primary antibodies were diluted in blocking solution and incubated with the samples overnight at 4° C. Samples were rinsed with PBS and incubated with the appropriate fluorescently labeled Alexa-Fluor secondary antibodies (Invitrogen 1:500) for one hour at room temperature. For nuclear staining, samples were incubated with 1 ug/ml DAPI (Sigma) for five minutes. The primary antibodies used were: Sox10 (R&D Systems, AF2864; 2 μg/ml), Olig2 (Millipore, AB9610; 1:1000), Nkx6.2 (Abcam, ab58708; 1 μg/ml), Sox1 (R&D Systems, AF3369; 1 μg/ml), Sox2 (R&D Systems, MAB2018; 1 μg/ml), Pax6 (Covance, PRB-278P; 0.67 μg/ml), Oct3/4 (Santa Cruz, SC-5279; 0.4 μg/ml), Nkx2.2 (DSHB, 74.5A5; 4.4 μg/ml), GFAP (DAKO, Z0334; 0.58 μg/ml), and MBP (Covance, SMI-99P; 2 μg/ml).

FACS and Flow Cytometry.

For PLP1:eGFP expression analysis, cells were lifted using TrypLE and rinsed 2× with OPC media without growth factors. Cells were analyzed on a FACSAria or LSR flow cytometer (BD Biosciences) and plots were generated with WinList 3D 7.0 software. Quadrant gates for fluorescence-activated cell sorting and flow cytometry were set with negative controls (uninfected MEFs) at less than 0.1% positive cells.

RNA Isolation and qPCR.

Cells were lysed in 1 ml TRIzol (Invitrogen) and stored at −80° C. until ready for use. Chloroform separation was enhanced with Phase-Lock Gel Tubes (5 Prime). The aqueous phase was collected and the RNA isolation completed with the RNeasy Plus Kit (Qiagen) according to the manufacturer's protocol. 400 ng of RNA was reverse transcribed with SuperScript III Reverse Transcriptase (Invitrogen) and qPCR was performed using 8 ng of cDNA with TaqMan Gene Expression Master Mix and TaqMan probes: Sox10 (Mm01300162_m1), Nkx6.2 (Mm00807812_g1), Olig1 (Mm00497537_s1), Nkx2.2 (Mm01275962_m1), Myt1 (Mm00456190_m1), ST18 (Mm01236999_m1), Gm98 (MRF) (Mm01194959_m1) and Olig2 (AJVI3GC, custom) on the 7300 Real-Time PCR System (Applied Biosystems). Endogenous Olig2 expression was detected in iOPCs using the Olig2 (Mm01210556_m1) TaqMan probe in which one primer sits outside of the CDS and therefore does not detect expression from the lentiviral vector. All expression data were normalized to Gapdh (Mm99999915_g1) and samples in which no expression was detected were given an arbitrary Ct value of 40. All analyses were performed with quadruplicate technical replicates for each of a minimum of three independent biological replicates. Relative expression levels were determined by calculating $2^{-\Delta\Delta Ct}$ with corresponding S.E.M.

Results.

The eight transcription factors were selected from the OPC/oligodendrocyte lineage list based on their known roles during oligodendrocyte development: Olig1, Olig2, Nkx2.2, Nkx6.2, Sox10, ST18, Gm98 (MRF), and Myt1 (collectively referred to as 8 TFs), and each gene individually was cloned into a doxycycline-inducible lentiviral vector. The 8 TF pool was used to infect mouse embryonic fibroblasts (MEFs) isolated from mice carrying the reverse tetracycline controlled transactivator (rtTA) as well as a modified PLP1:eGFP transgene expressed specifically in both OPCs and oligodendrocytes. The PLP1:eGFP/rtTA MEFs were carefully isolated to be free of all neural tissue as demonstrated by the lack of neural stem cell, neuronal, astrocytic, OPC, and oligodendrocytic markers when assayed by immunostaining, qPCR, microarray, and flow cytometry. For all experiments, the percentage of cells infected was monitored by immunostaining for the individual transcription factors as well as induction level of the transgenes as measured by qPCR. Typically 30-60% of cells were infected with an individual factor and therefore only a small proportion of cells received all factors when infecting with multiple viruses; however, infection and induction (+doxycycline, +Dox) of the MEFs with the 8 TF pool consistently resulted in a large percentage (~13%) of cells expressing the OPC/oligodendrocyte-specific PLP1:eGFP transgene by day 21 when cultured in OPC-promoting culture conditions containing FGF2, PDGF-AA, and sonic hedgehog (SHH). Uninfected (No TFs) and uninduced (-Dox) PLP1:eGFP MEFs cultured under identical conditions did not contain GFP+ cells.

The number of transcription factors necessary for the generation of PLP1:eGFP+ cells (designated as induced OPCs, iOPCs) was then narrowed down. Individual factors from the 8 TF pool were removed and revealed that 7 TF pools lacking either Sox10, Olig2, or Nkx6.2 had large decreases in the percentage of PLP1:eGFP+ cells at day 21; indicating that these genes are required for efficacious reprogramming (see FIG. 2a).

Figure 2B:
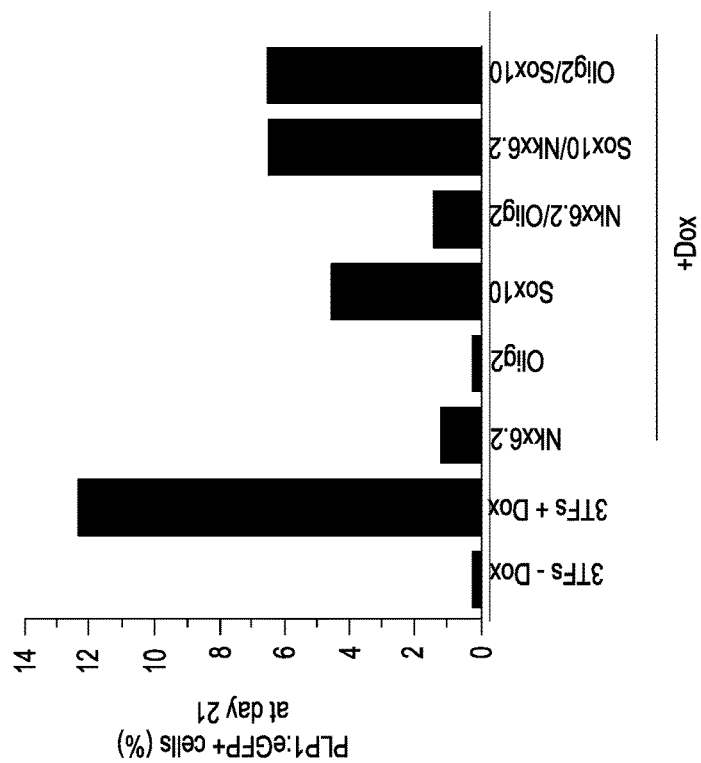
FIG. 2 A-E are graphs of results obtained from performing methods according to the present invention.
Figure 2A:
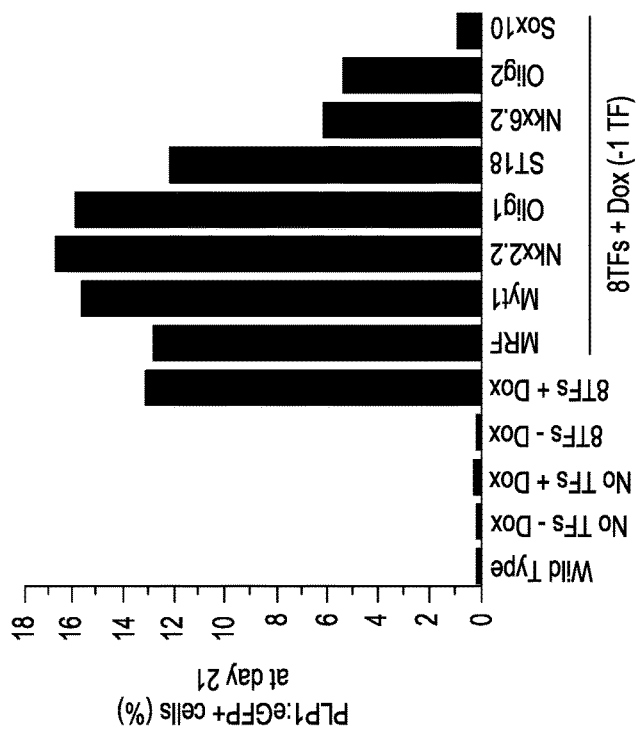
Figure 2D:
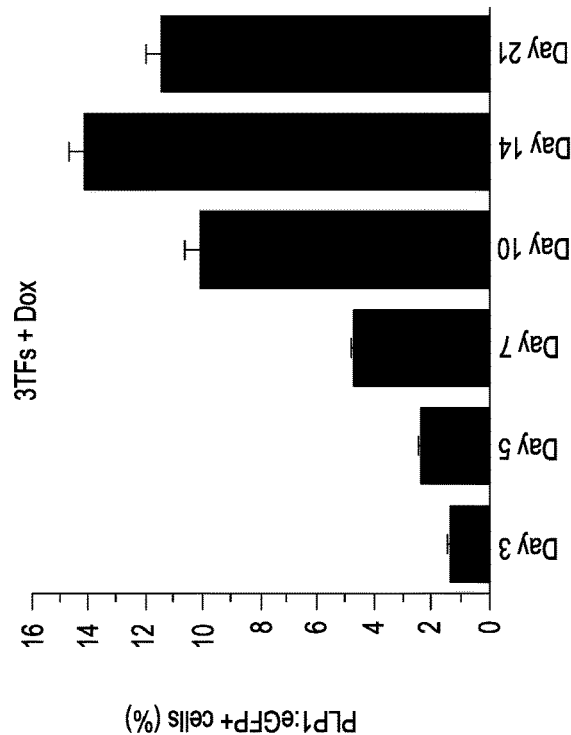
Figure 2C:
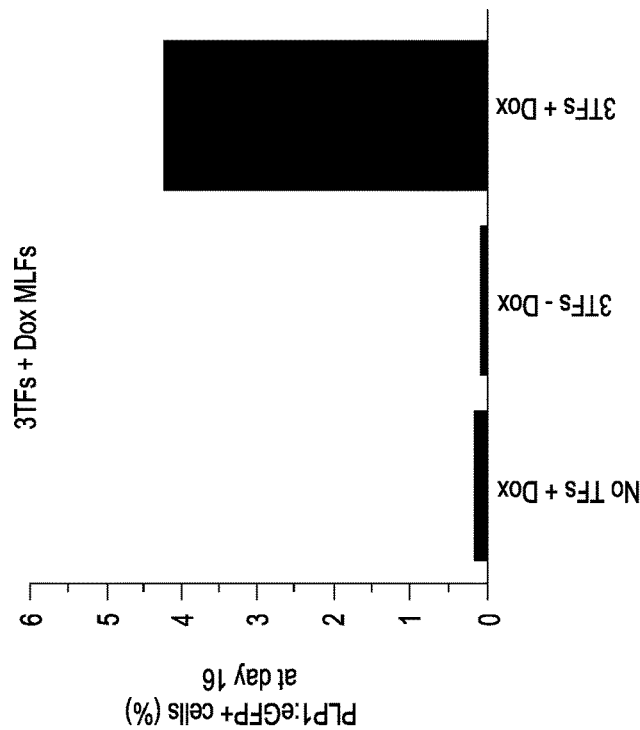

To further test this result, Sox10, Olig2, and Nkx6.2 (collectively referred to as 3 TFs) were expressed in MEFs and results showed that these three factors were sufficient to produce iOPCs at levels equivalent to 8 TFs (compare FIGS. 2a and 2b). It was then investigated whether Sox10, Olig2, or Nkx6.2 individually or in pairs would be adequate to produce iOPCs. It was found that the percentage of PLP1:eGFP+ cells decreased with any variation from the 3 TF pool, indicating that these three genes were both necessary and sufficient for efficient iOPC generation from MEFs (see FIG. 2b). Importantly, these 3 TFs were also able to induce the production of iOPCs from an alternate somatic cell source, mouse lung fibroblasts (see FIG. 2c).

To view the kinetics of iOPC production, flow cytometry was performed at intervals throughout the 21-day induction period. A low percentage of PLP1:eGFP+ cells was detected within 5-7 days after induction, but the percentage dramatically increased between days 7-10 and leveled off for the remainder of the induction period (see FIG. 2d). These results suggested that the reprogramming process was complete within 7-10 days. To further test this, the minimal induction period required for the generation of iOPCs was investigated. Again, a major shift in the percentage of iOPCs was seen between days 8-10 of induction indicating that exogenous factor expression is required for approximately 8-10 days to efficiently generate iOPCs from MEFs (FIG. 2e).

Next it was investigated whether the iOPCs exhibited cellular and molecular features consistent with those of bona fide OPCs. In vivo, OPCs first emerge from the ventral ventricular zone of the developing spinal cord and characteristically display a bipolar morphology, proliferate in response to PDGF and FGF, express a defined set of oligodendrocyte lineage genes, and differentiate into oligodendrocytes in response to growth factor withdrawal and exposure to thyroid hormone (T3). The iOPCs exhibited a bipolar morphology and could be expanded at least five passages in culture giving rise to millions of iOPCs. Further, global gene expression profiles of the iOPCs showed clear down regulation of the MEF-specific program and activation of genes specific to the oligodendrocyte lineage such as Nkx2.2, Olig1, and Olig2. Since many OPC-specific genes were also in the transcription factor pools, it was confirmed that the endogenous gene Olig2 was activated using specific qPCR primers. Gene expression changes during the reprogramming of MEFs to iOPCs were further investigated using GREAT (Genomic Regions Enrichment of Annotations Tool) 25. GREAT analysis of genes up-regulated during the conversion of MEFs to iOPCs showed significant association with 'Gene Ontology (GO) biological processes' such as "myelination" ($p=7.75\times10^{-8}$) and "gliogenesis" ($p=4.19\times10^{-5}$), 'MGI (mouse genome informatics) phenotype ontologies' such as "oligodendrocyte morphology" ($p=2.98\times10^{-10}$) and "glial cell morphology" ($p=3.52\times10^{-7}$), and 'MGI expression ontologies' such as "TS22 spinal cord; lateral wall; ventricular layer" ($p=5.77\times10^{-5}$). Genes down-regulated during the conversion of MEFs to iOPCs showed significant association with a large number of mesodermal processes consistent with the inactivation of the global fibroblast gene expression program. Combined, these results indicate that the expression of defined sets of transcription factors in MEFs can globally repress fibroblast-specific genes and activate gene expression programs and cellular and molecular features consistent with authentic OPCs.

It was demonstrated that iOPCs could differentiate into oligodendrocytes in response to growth factor removal and the addition of T3 in vitro. Strikingly, iOPCs were capable of differentiating into 'induced oligodendrocytes' (iOLs) within 2-3 days using either 8 TF or 3 TF. iOLs exhibited a multiprocessed morphology typical of oligodendrocytes and expressed myelin basic protein (MBP), an integral protein component of the myelin sheath. iOPCs could be frozen/thawed and expanded for multiple passages while still maintaining the ability to differentiate into MBP+ iOLs. Quantification of MBP+ iOLs revealed that the iOPCs were a heterogeneous mixture of cells; however, while the efficiency of iOL generation was low, iOLs were only generated by cells infected and induced with 8 TF or 3 TF pools. Uninfected or uninduced fibroblasts never gave rise to oligodendrocytes.

Example 2: In Vitro Myelination by Fibroblast-Derived OPCs

Myelination Analysis.

The forebrain and cerebellum of early postnatal (P5) shiverer (C3Fe.SWV-Mbpshi/Mbpshi; Jackson Laboratory) or wildtype mice were dissected and 300 μm slices produced on a Leica Vibratome. Slices were cultured as described in Mi, et al., Ann Neurol, 65:304-15 (2009) in a DMEM/BME base with 15% Horse serum, Hong's N2 and PDGF-AA for three days. 5×104–2×105 iOPCs were manually injected with a pulled glass pipette into each slice and grown for an additional 10 days in culture. Slices were then fixed in 4% paraformaldehyde, treated with ice cold 5% acetic acid/95% methanol, and assayed for MBP expression (Covance, SMI99; Jackson Labs, Biotin-anti-mouse IgG; Vector Labs, ABC; Sigma, DAB; or Alexa594 secondary antibody, 1:500).

Results.

The function of iOPCs was further investigated by testing the ability of the iOPCs to myelinate axons of hypomyelinated shiverer (MBPshi/shi) mice, which completely lack MBP and compact myelin 28. iOPCs were injected into organotypic slice cultures of early postnatal shiverer forebrain or cerebellum where they clearly colonized and aligned along white matter tracts. Importantly, within 10 days a number of iOPCs generated MBP+ myelin sheaths. In summary these data clearly demonstrate that functional iOPCs can be produced by modulating defined sets of transcription factors in fibroblasts. The iOPCs are expandable in culture and have the ability to myelinate axons of hypomyelinated mice.

Example 3: In Vivo Myelination by Fibroblast-Derived OPCs

Myelination Analysis.

PAST TENSE!!!The shiverer mutant mouse is used as a model system to demonstrate in vivo remyleination using the mesodermal cell-derived OPCs of the present invention. Congenitally hypomyelinated shiverer mice fail to generate compact myelin and die by 18-21 weeks of age. The model used is as described in U.S. Pat App. No. 20080206209 and Windrem et al., Cell Stem Cell 2, 553-565, June 2008, both of which are incorporated by reference in their entirety.

Briefly, early post-natal (P1-P3) shiverer (Mbpshi/shi) mice serve as a host for the transplantation of fibroblast cell-derived OPCs produced as described in Example 1. Pups are anesthetized with isofluorane and 1.5 ul of a 167,000 cells/μl suspension in neural base medium is injected unilaterally to target the future corpus collosum. Injections are performed through the skull with a Hamilton syringe to a depth of 1.5 mm.

Mice injected with fibroblast-derived OPCs as well as wild type mice and control mice injected with vehicle only (sham-treated mice) are sacrificed at various time points to analyze myelination. Pups are anesthetized with Avertin and perfused. The brains of both OPC-treated and sham-treated mice are fixed, sectioned, and stained for myelination as per Windrem et. al., Cell Stem Cell., 5; 2(6):519-20 (2008).

The OPCs derived from the fibroblasts demonstrate an ability to partially or fully rescue the shiverer phenotype, depending upon dosage of the cell population used.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. § 112, ¶16.

We claim:

1. A method of promoting myelination in the central nervous system (CNS) of a subject in need thereof, the method comprising directly administering at a site within the CNS of the subject a therapeutically effective amount of an isolated population of reprogrammed glial cells, thereby enhancing myelination at the site of administration, wherein the isolated population of reprogrammed glial cells is generated by:
   providing somatic cells from the subject;
   culturing said somatic cells;
   infecting somatic cells with a retroviral vector to deliver reprogramming factors Sox 10, Olig2, and Nkx6.2;
   inducing expression of reprogramming factors Sox 10, Olig2, and Nkx6.2 in said cultured somatic cells under conditions to reprogram the somatic cells into a population of glial cells, wherein the glial cells express endogenous gene Olig2; and
   sorting said population of re-programmed glial cells from non-programmed cultured somatic cells to produce an enriched population of re-programmed glial cells.

2. The method of claim 1, further comprising infecting said somatic cells with a retroviral vector to deliver one or more additional reprogramming factors selected from Olig1, Nkx2.2, ST18, MYT1 or GM98; and inducing expression of one or more additional reprogramming factors selected from Olig1, Nkx2.2, ST18, MYT1 and GM98 in said cultured somatic cells.

3. The method of claim 1, further comprising infecting said somatic cells with a retroviral vector to deliver at least three additional reprogramming factors selected from the group consisting Olig1, Nkx2.2, ST18, MYT1 and GM98; and inducing expression of at least three additional reprogramming factors selected from the group consisting Olig1, Nkx2.2, ST18, MYT1 and GM98 in said somatic cells.

4. The method of claim 1, wherein the retroviral vector comprises an inducible promoter.

5. The method of claim 4, wherein said retroviral vector further includes a selectable marker.

6. The method of claim 1, wherein said somatic cells are fibroblasts, hematopoietic cells, adipocytes or chondrocytes.

7. The method of claim 6, wherein the cultured somatic cells are fibroblasts able to produce a population of oligodendrocytes and oligodendrocyte progenitor cells (QPCs).

8. The method of claim 1, wherein said sorting step is accomplished by using one or more markers specific for glial cells.

9. The method of claim 8, wherein said one or more markers are selected from the group consisting of PLP-I, myelin basic protein (MBP), A2B2, A2B5, nextin, platelet-derived growth factor alpha receptor, SOX10, Olig1, chondroitin sulphate proteoglycan NG2, myelin-associated glycoprotein, myelin oligodendrocyte glycoprotein, or galactocerebrosides O1 or GalC.

10. The method of claim 1, further comprising a step of expanding said population of re-programed glial cells after said expressing step.

11. The method of claim 1, wherein one or more of the reprogramming factors are expressed from one or more exogenous genes in the somatic cells.

12. The method of claim 1, wherein at least 5% of said population of somatic cells are glial cells.

13. The method of claim 12, wherein at least 10% of said population of somatic cells are glial cells.

14. The method of claim 1, wherein the subject has a neurodegenerative disease.

15. The method of claim 14, wherein the subject has multiple sclerosis.

* * * * *

UNITED STATES PATENT AND TRADEMARK OFFICE
CERTIFICATE OF CORRECTION

PATENT NO. : 10,119,123 B2
APPLICATION NO. : 15/346453
DATED : November 6, 2018
INVENTOR(S) : Tesar et al.

It is certified that error appears in the above-identified patent and that said Letters Patent is hereby corrected as shown below:

In the Specification

Immediately following the section header "STATEMENT OF GOVERNMENT SPONSORED RESEARCH", at Lines 17-19 of Column 1, please replace the paragraph below:
*This invention was supported in part by grant R21MH087877-01 from the National Institute of Mental Health (NIMH).*

With the following paragraph:
*This invention was made with government support under grant number MH087877 awarded by the National Institutes of Health. The government has certain rights in the invention.*

Signed and Sealed this
Twenty-third Day of July, 2019

Andrei Iancu
*Director of the United States Patent and Trademark Office*